United States Patent [19]
Ritter et al.

[11] Patent Number: 5,654,864
[45] Date of Patent: Aug. 5, 1997

[54] CONTROL METHOD FOR MAGNETIC STEREOTAXIS SYSTEM

[75] Inventors: Rogers C. Ritter, Charlottesville, Va.; Michael A. Lawson, Livermore; Robert G. McNeil, Menlo Park, both of Calif.

[73] Assignees: University of Virginia Patent Foundation, Charlottesville, Va.; Stereotaxis, Inc., Menlo Park, Calif.

[21] Appl. No.: 280,124

[22] Filed: Jul. 25, 1994

[51] Int. Cl.⁶ .................................................. H02N 15/00
[52] U.S. Cl. ........................ 361/141; 361/143; 361/146
[58] Field of Search ........................................ 361/141, 143, 361/144, 145, 146

[56] References Cited

U.S. PATENT DOCUMENTS

| | | | |
|---|---|---|---|
| 2,856,238 | 10/1958 | Dacus | 361/143 X |
| 4,869,247 | 9/1989 | Howard, III et al. | |
| 5,030,196 | 7/1991 | Inoue | 361/143 X |
| 5,093,754 | 3/1992 | Kawashima | 361/144 |
| 5,125,888 | 6/1992 | Howard et al. | |
| 5,150,272 | 9/1992 | Danley et al. | 361/144 |
| 5,267,091 | 11/1993 | Chen | 361/141 X |
| 5,332,987 | 7/1994 | Hennessy et al. | 361/144 X |
| 5,359,490 | 10/1994 | Oguro | 361/144 |

*Primary Examiner*—Fritz Fleming
*Attorney, Agent, or Firm*—James Creighton Wray

[57] ABSTRACT

A control method permits the operation of multiple superconducting magnetic coils so as to move a magnetic object to precisely specified locations within the body under command of a physician-operator observing the motion with live fluoroscopic imaging fused with more detailed preoperative imaging of some other kind. A computer contains the preoperative images and the fluoroscopic images, as well as the means to effect changes in the coil currents so as to accomplish the desired magnetic object motion and positioning. The control method operates the coils in pairs on opposite sides of the body in a manner to minimize the necessary current changes, thus avoiding the quenching of the superconducting coils. Combinations of these pairs can execute motion of the magnetic object in any direction in an impulsive manner and with high precision. The method should function well and provide advantages with coils which are not superconducting as well. The method overcomes the redundance present in the limited constraints given by a simple movement vector by the physician-operator.

37 Claims, 4 Drawing Sheets

Control Method for Magnetic Stereotaxis System

BACKGROUND OF THE INVENTION

This invention relates to an apparatus for delivering treatment to a specific location in a portion of the body and the method of using this apparatus to achieve this treatment delivery. Specifically, this invention relates to the method, usually written in software for a computer, for controlling currents in coils, which create a force on a magnetic object to achieve this treatment delivery to the specific location in the body part.

Present methods of controlling the current in multiple-coil force mechanisms usually employ linear methods. That is, power supplies or amplifiers supplying the coil currents act in a direct or a feedback mode to cause the desired magnetic effect in response to some manner by which the effect is detected. This method is often termed the "servo amplifier" method. Two examples are the control of magnetically suspended models in wind tunnels, and the control of magnetically suspended shafts in magnetic bearings.

When the coils have large inductance, the amplifiers and/or power supplies which supply the currents must be capable of delivering large amounts of power in order to change the currents with sufficient rapidity to maintain control of the forces on the magnetic objects. Added to this is the difficulty encountered with superconducting coils, which may quench when the current is changed rapidly. Quenching is the process in a superconducting magnet by which the coil loses its superconductivity and the very rapid power increase boils out much of the liquid helium which is the cooling element of the coil. As a result, superconducting coils are seldom operated in a manner in which the current changes significantly in a short time.

A need exists for a precise control system for stereotaxis systems.

SUMMARY OF THE INVENTION

The invention described below uses particular relationships between the currents in the various coils, as well as particular time relationships of the currents in the coils to enable control of the magnetic object in small, accurate steps, while avoiding quenching of the coils.

While the present invention can be used with any superconducting coil force system, it has been tested and used with one embodiment of the magnetic stereotaxis system (MSS) of U.S. Pat. Nos. 4,869,247, Video Tumor Fighting System and 5,125,888, Magnetic Stereotactic System for Treatment Delivery. This embodiment is a cubic array of six superconducting coils moderately foreshortened in one dimension.

The method of this invention is based on the use of multiple coils. While the full method modifies the following in a way described later, it is most directly understood on consideration of the effects of a single coil pair and with the magnetic object on their common axis. For each coil pair, one member is the main, or pulling coil, and the other is the supplemental or subsidiary, or pushing coil. It is the nature of coils that the magnetic field has the same direction on the two sides of the plane of the coil, while the gradient has the opposite directions. This can be seen in FIG. 1 for either of the coils independently. For example, the field B1 and gradient G1 result from current in coil 1. Likewise B2 and G2 result from current in coil 2. The force on a magnetic object is proportional to the gradient of the field at the location of the object. The direction of the moment of the magnetic object gives the direction of the force on it, caused by the gradient of the field. At the same time, the direction of the moment of the magnetic object is governed by and parallel to the direction of the magnetic field, in soft tissue. Thus the relative directions of the currents in the two coils of a pair control these relationships.

An overriding need for an effective coil system is that the necessary force on small magnetic objects be sufficient to overcome the resistance of the body material in which it is immersed. In this invention we obtain much larger force by using coil pairs with currents in opposite directions, sometimes called the "anti-Helmholz" arrangement. FIGS. 1a and 1b indicate both the Helmholz and the anti-Helmholz arrangements. Shown are the individual magnetic fields and gradients of the two coils, along their common axis, and their combined fields and gradients. This is shown for equal magnitudes or current in the two coils, although in use of the present invention the currents are usually not equal.

The first practical aspect of this arrangement with currents of equal magnitudes is that only the closest coil of the pair can pull the magnetic object. If the magnetic object is a permanent magnet, it can be oriented initially so that the closest coil would tend to push it, but in practice, the object will not be stable in this orientation, and in soft tissue will reverse its direction before significant force is applied.

In the method of this invention the currents are generally not equal. The case of most difficulty is when the magnetic object must be pulled from the far side of the head. In this case the largest current is in the coil which is farthest from the magnetic object; this is the "main" coil, and it pulls the magnetic object. A smaller current is in the coil closest to the magnetic object, the amount depending on its relative distance to each of the two coils. The current in the pushing coil must always be small enough that the contribution of magnetic field from it will not be as large as the contribution of magnetic field from the coil which must pull the magnetic object. Otherwise, the magnetic object will reverse its orientation and move in a direction opposite the desired one. The fact that the magnetic field essentially falls off inversely as the cube of the distance from the coil, while the gradient falls off inversely as the fourth power of the distance from the coil, facilitates this arrangement. When the magnetic object is quite far from the pulling coil, it can still exert a dominant orienting magnetic field, while the much closer coil with much smaller current can exert the dominant gradient, hence force, in the correct direction. Such an improvement is possible, even when the current in the pushing coil is kept below the magnitude at which it would reverse the magnetic object orientation.

A second aspect of this invention is the control of the magnetic object motion by specially controlled impulsive forces which give precise steps to the motion. In this method, the force impulse on the magnetic object from the coil pair in question has two parts: one is the relatively constant force from the main, pulling coil, the other is a force of short duration from the subsidiary, pushing coil. This step is called "boost". Under the most stringent conditions, the typical maximum current in the subsidiary coil (maximum boost current) is 15% of the maximum in the main coil. Such a condition, allowed by the aforementioned difference in the distance dependence of the magnetic field and its gradient, can be thought of as a leverage in the activity of the subsidiary coil, in relation to the current, and how it limits ramping rates which are possible without quenching the coil. This enables the application of ramping its current up and down in a much shorter time than would be possible with the main coil. The combined forces of the main coil and the subsidiary coil create an impulse sufficient to move the magnetic object a short and specified distance, if calibrated to the material of the body in which the object moves.

A third element in our control system allows for a mode of operation in which the subsidiary coil has its current reversed briefly, causing it to pull back on the magnetic object, in effect cancelling the impulse which started the motion. This step is called "halt", and the subsidiary current during the step is called "halt current". During this period the two coils are acting in the Helmholz mode. When motion is in certain regions of the space between the two coils, even a short step of motion will put the magnetic object enough closer to the main, pulling coil so that the magnetic object might not totally cease its motion at the end of the impulse from the subsidiary coil. This is the case even when the main coil current is reduced as the magnetic object moves towards it, because the large current in the main coil cannot be reduced fast enough without risk of quenching it. Thus the subsidiary coil in halt mode acts to retard motion while the main coil current is being further reduced to below the threshold for a moving force on the magnetic object.

This explanation of the motion on the axis of one coil pair is exact. When the magnetic object is off the axis, or when more than one coil pair is energized, the same concept applies to members of the combinations, but with approximations to be described below.

A fourth element in this invention is the combination of forces from several coil pairs, in an algorithm which allows interactive control to overcome the lack of sufficient other input information. In one application there are three pairs of coils, along mutually perpendicular axes, acting to move a magnetic object in the brain. The effects of each coil pair are added in an approximate manner, which can be tested against a firm calculation of the effects of currents in the combined coils. If the calculated result differs too greatly from the intended, the operator can make changes to reduce the difference. In this manner the inverse problem of electromagnetism is handled by the iteration of a called-for motional distance, the assumption of currents needed to develop the force impulse to give a motional distance step in an oversimplified model, the comparison of the motion to be expected from the calculated force impulse from the assumed currents, and an operator comparison of the actual result of the assumptions with the result intended at the outset. The inverse problem of electromagnetism is the problem in which a given field and/or gradient is needed at a point or region, and the problem is to find the sources needed to create that field and/or gradient. By contrast, the direct problem of electromagnetism is simpler: given one or more sources, what is the field and/or gradient at a point or region? The reason the inverse problem is often more difficult is that a particular design of sources (in the present case coils) will require more information than just the field and/or gradient.

An essential element in this application is the production of positional information about the magnetic object before the start of each step. At present this information is developed from biplanar fluoroscopy, but other means could be used. The method is called the Vector Approximation, or Vector Method, and the manner in which this is accomplished is seen in the following description of an example of using the magnetic stereotaxis system (MSS) for moving a magnetic object in the brain.

The difficult conceptual part of any magnetic force application program for the six-coil version of the MSS is in dealing with the inverse problem of electromagnetism defined above. In this example, the needed force (a vector with three independent components) is given by the physician-operator, and to provide the force one must find the currents for the six coils which will efficiently provide the gradient at the magnetic object to accomplish that force. For a definite and direct mathematical solution we need a total of six independent input conditions, not just the three force vector components. This requires additional constraints involving some very subtle judgment concerning electromagnetic theory. Several added concepts can be introduced and built into an algorithm which has six equations in the six unknown currents. But the added concepts and equations must be chosen so as not to violate certain practical conditions. For example, a set of three additional equations can be written for the magnetic field components at the location of the magnetic object. Physically, these can be introduced into the solution by requiring that the magnetic field direction be the same as the force direction. However, it can be readily shown that there are regions for the magnetic object, within the coil system, for which this condition requires huge currents in some of the magnets in order to produce small forces. The way the present method avoids this requirement for added information is by approximating the electromagnetic force needed from an input directive on a motional step, then calculating the actual resulting force and the ensuing motional step. From displays of the consequences of these calculations the operator can then judge whether to, and by how much to modify particular coil currents so as to reach acceptable accuracy.

A combination of vector input and displayed vector calculation is a feasible approximation which constitutes the force decision part of the motion-force algorithm described here. Motion of the magnetic object occurs in successive steps, each of which is controlled by this algorithm. This has human input at the start of each motional step: the initial magnetic object direction and distance step command from a mouse or joy stick, displayed on screen as, for instance, a red arrow. Specific to the present algorithm is a second human input segment of the control loop: judgment and revision (before execution) when compared with the actual step motion expected from the command as executed by the Vector method. A comparison of two arrows, desired move (e.g. red) and "actual" move (e.g. green) allow the judgment. In this process the algorithm calculates needed magnet current levels (with some error) based on the direction and length of the red arrow, and the user can revise the current levels appropriately. It then calculates the actual force which these currents will apply, and using a previously measured force-to-distance transfer function will present the distance and direction to be traveled as the green arrow. It will be recognized that this green arrow calculation is the regular problem of electromagnetism, and need not require any approximation.

What is meant by the Vector Method is that each component of the needed gradient is calculated from currents in the coils for that axis only. Thus the x-component of the gradient, $G_x$, uses only the x-axis coils, $G_y$ uses only the y-axis coils, and $G_z$ uses only the z-axis coils. With techniques to be discussed below, this permits direct calculation of the inverse problem, but it ignores the curvature of the field lines. Since the actual motional region is relatively a small part of the total volume (within a spherical region less than 20 cm diameter) as compared with the rectangular volume determined by the coil sizes and inter-coil distances (61 cm in this example), the approximation would be expected to be moderately successful, and tests show that to be the case for these dimensions.

Implicit in the algorithm is the use of the mechanical Distance-to-Force Impulse Transfer Function (DF Trans Fncn) to provide the temporal qualities of the impulse. Nothing else in the algorithm until the very end, where boost logic comes into play, considers any time-dependence. Also implicit in the algorithm is that boost operation is ignored until this last step. These assumptions need involve no approximation, but must be treated empirically. This is the point where results from previous actual experiments are used, and their effectiveness depends heavily on having used a good, representative phantom material.

A control method permits the operation of multiple superconducting magnetic coils so as to move a magnetic object to precisely specified locations within the body under command of a physician-operator observing the motion with live fluoroscopic imaging fused with more detailed preoperative imaging of some other kind. A computer contains the preoperative images and the fluoroscopic images, as well as the means to effect changes in the coil currents so as to accomplish the desired magnetic object motion and positioning. The control method operates the coils in pairs on opposite sides of the body in a manner to minimize the necessary current changes, thus avoiding the quenching of the superconducting coils. Combinations of these pairs can execute motion of the magnetic object in any direction in an impulsive manner and with high precision. The method should function well and provide advantages with coils which are not superconducting as well. The method overcomes the redundance present in the limited constraints given by a simple movement vector by the physician-operator, an effect of the "inverse problem of electromagnetism". Namely, when there are more than three coils acting at one time, the specification of the required three currents is not fully met by the stipulation of the three directional components of a specified motion step.

These and further and other objects and features of the invention are apparent in the disclosure, which includes the above and ongoing written specification, with the claims and the drawings.

DETAILED DESCRIPTION OF THE DRAWINGS

Figure 1A:
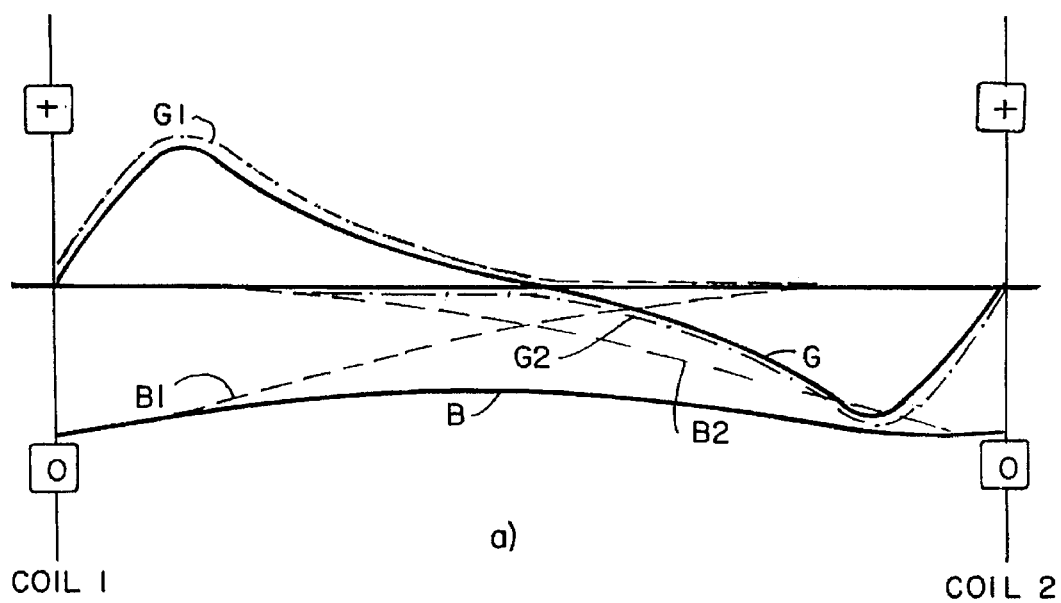
FIGS. 1a and 1b are schematic diagrams of the magnitudes and directions of the magnetic field B and the gradient G along the axis between two coils having currents of equal magnitudes but in opposite directions (anti-Helmholz, FIG. 1b), and for currents in the same directions (Helmholz, FIG. 1a).
Figure 1B:
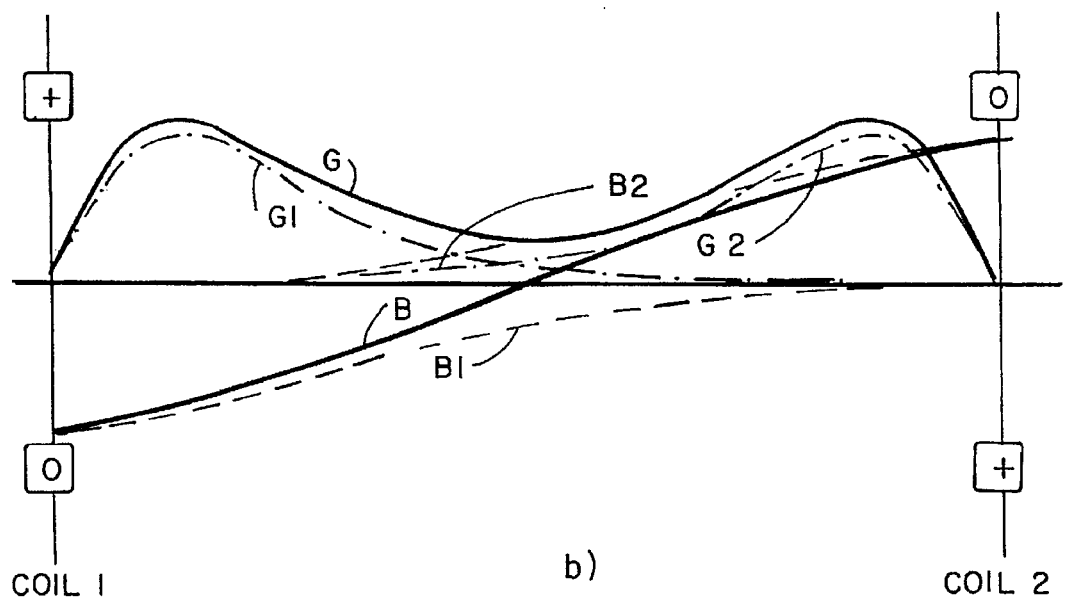

FIGS. 1a and 1b show the two classical arrangements of a pair of coils having a common axis, and with equal current magnitudes. The present control method is built upon using the second arrangement, as shown in FIG. 1b.

FIG. 1a shows a Helmholz arrangement. The current in the coils is shown as o for out of the paper and + for into the paper. The magnetic fields and gradients along the axis are shown. B1 and B2 are the magnetic fields contributed by coils 1 and 2, respectively. G1 and G2 are the gradients of those fields, respectively. B and G are the algebraic sums of those magnetic fields and gradients. In that arrangement the magnitudes of the individual magnetic fields add, while the magnitudes of the gradients subtract.

FIG. 1b shows an anti-Helmholz arrangement. Symbols are the same as shown in FIG. 1a. Here can be seen that the magnitudes of the magnetic fields subtract, while the magnitudes of the gradients add.

Figure 2:
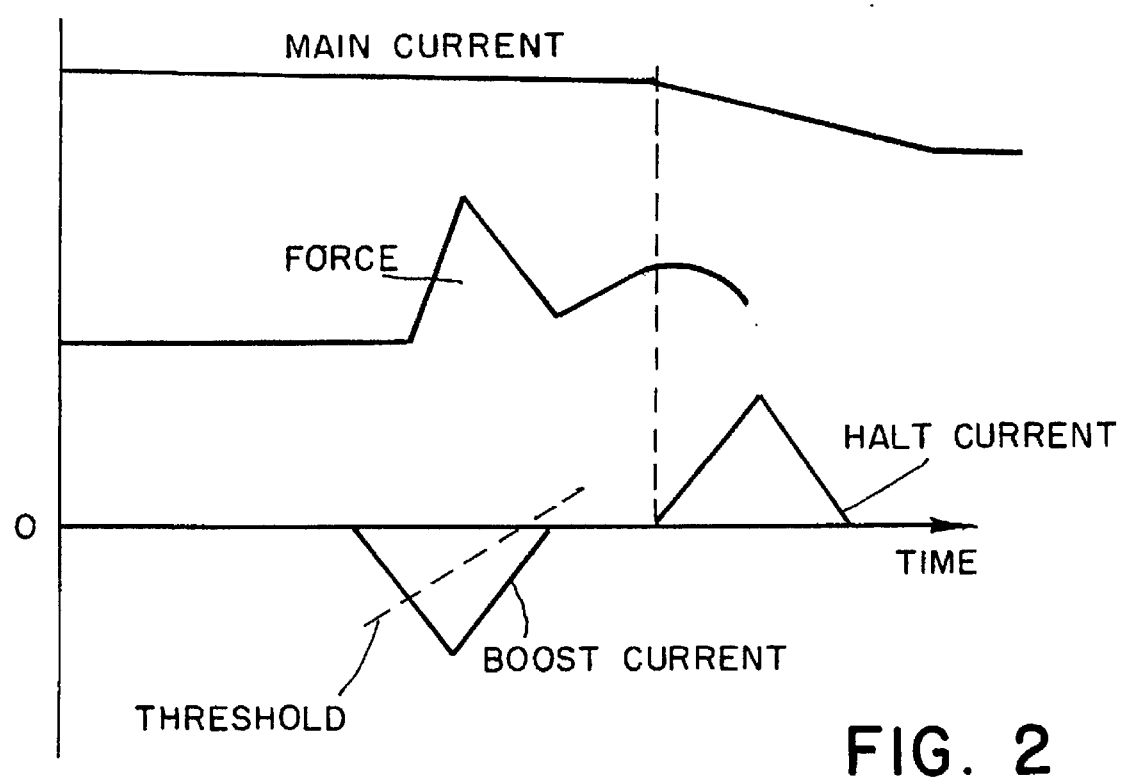
FIG. 2 is a schematic diagram of the progression in time of the currents in two coils acting as a pair in the manner described, and the force on a magnetic object at a representative point between them. These illustrate the action of the two coils. The main coil produces a sub-threshold force and the subsidiary coil produces a boost, initially to cause magnetic object movement, and finally to halt the movement.

FIG. 2 illustrates the currents and force on the magnetic object as a function of time during the typical operation of a pair of coils for one step of motion. The main coil current is steady until the start of the "halt" or retarding part of the motion cycle. At that time it is ramped to a lower quantity so that the magnetic object, at its new position, will not continue to move. The boost or halt currents in the supplemental or subsidiary coil are roughly triangular ramps in time, providing impulsive additions to or subtractions from the nearly steady force due to the main coil. Although it is not the case for every position of the magnetic object in the head, sometimes its change in position during the boost part of the cycle will place it so that the main current alone is sufficient to exceed the threshold force for motion. That situation is depicted by the dashed line showing threshold. It shows that under such a case the force rises even after the boost current is off, and the magnetic object keeps moving, in a condition called runaway. For that reason, the halt part of the cycle is started at some time after the boost finishes, which reduces the total force below threshold and stabilizes the position of the magnetic object. During the boost cycle the coils are in the anti-Helmholz configuration and during the halt motion the coils are in the Helmholz configuration.

Figure 3:
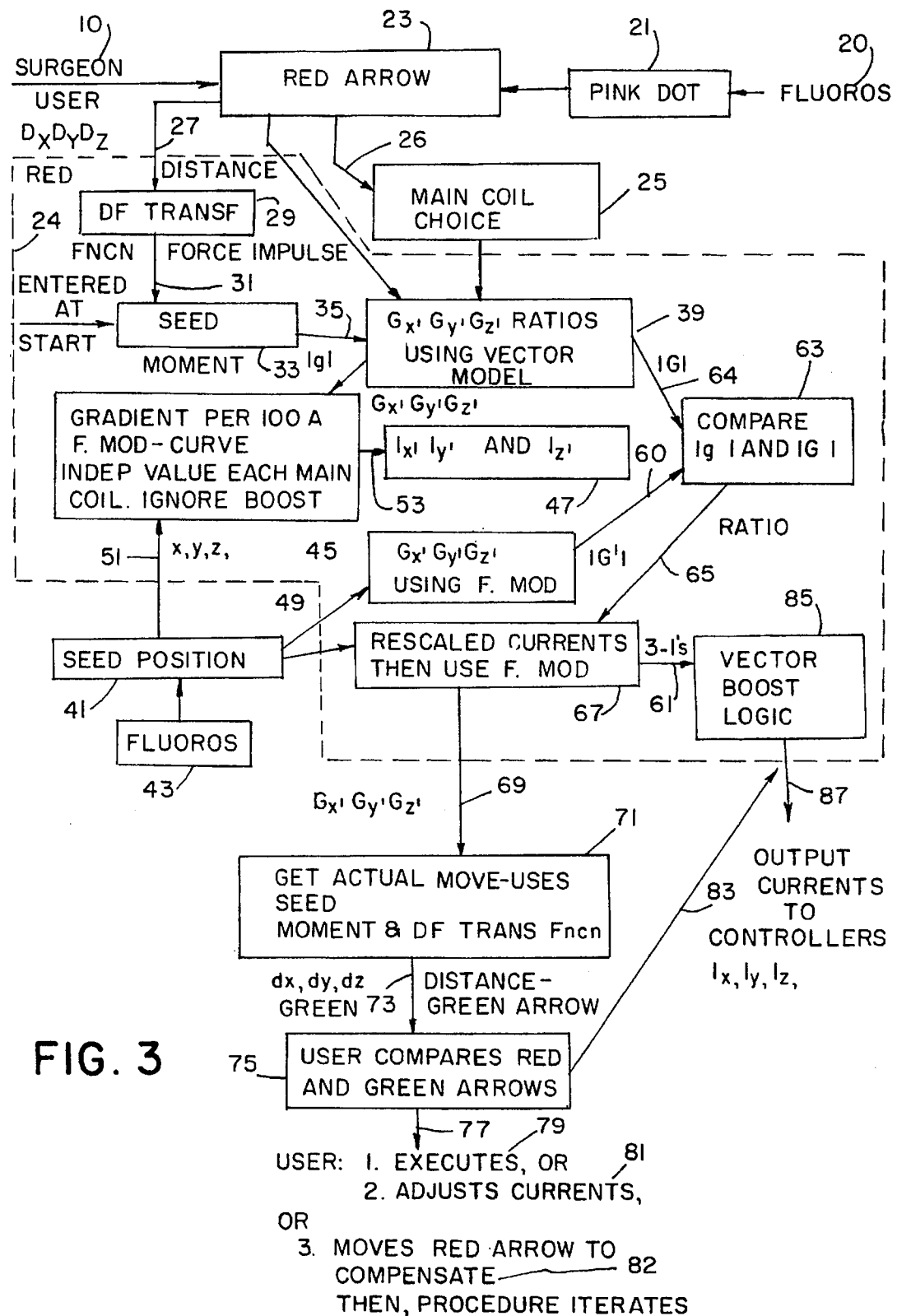
FIG. 3 is a block diagram showing the interaction of various parts of the algorithm which accomplishes the motional step of the magnetic object in one embodiment of the MSS.

FIG. 3 is a block diagram of one mode of using the features discussed in this invention in a computer program to control the set of three coil pairs. The operational details of this diagram are discussed in the algorithm steps below. The following is an example of how this system works. Although this example describes using this method for moving an object in the brain, this method is easily adapted for use with other body parts.

Figure 4:
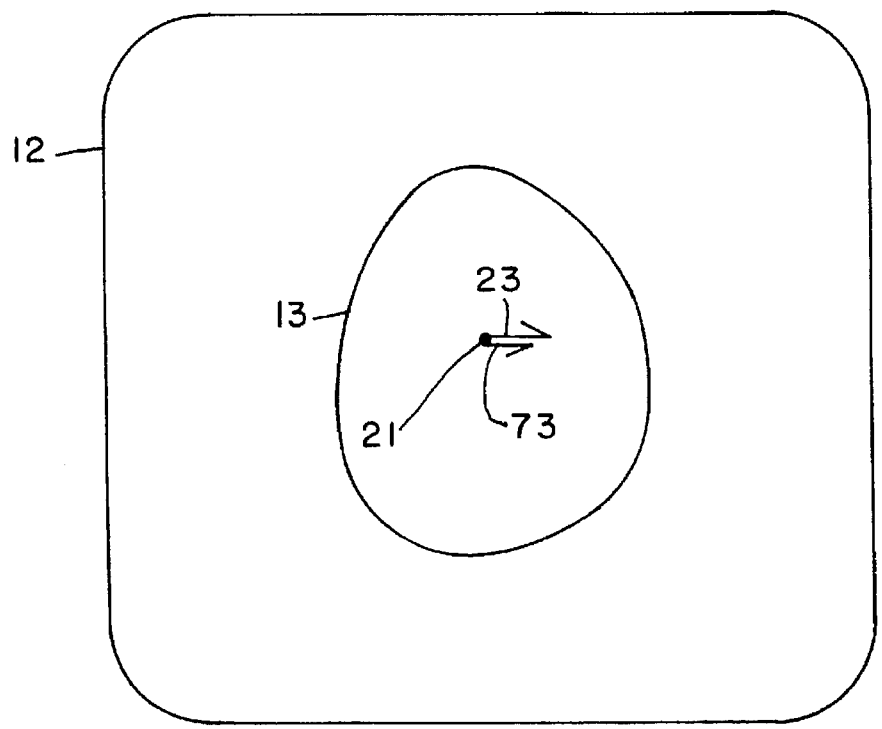
FIG. 4 schematically shows a computer screen.

Initially, for each step of a procedure using this method, as shown in FIGS. 3 and 4, the surgeon 10 views the present magnetic object position 21 on the computer screen 12. The object position is shown superposed on the appropriate preoperative MR/CT scan 13. The magnetic object location has been mathematically determined from the biplanar fluoroscope images 20, and then superimposed as a symbol (e.g., a pink dot 21) on the MR atlas pages on the screen. The user then inputs the vector position change desired for the seed as the next step. This is shown as the red arrow 23.

The algorithm 24 operates on that information as follows:
1. Chooses which are the three main coils 25 from the vector components 26 of the red arrow.
2. From the length 27 of the arrow, combined with the DF Trans Fncn 29, calculates the force impulse 31 needed to travel that distance. At this stage there is an implicit assumption about the time-dependence of the impulse contained within the DF Trans Fncn, which is actually a distance-to-force impulse transfer function.
3. With the (input) value of the seed magnetic moment 33, it calculates the gradient (impulse) magnitude 35 corresponding to that force impulse magnitude.

4. From the direction cosines 37 of the red arrow (rotated from screen coordinates to coil coordinates) it calculates the gradient impulse components 39.

Figure 5:
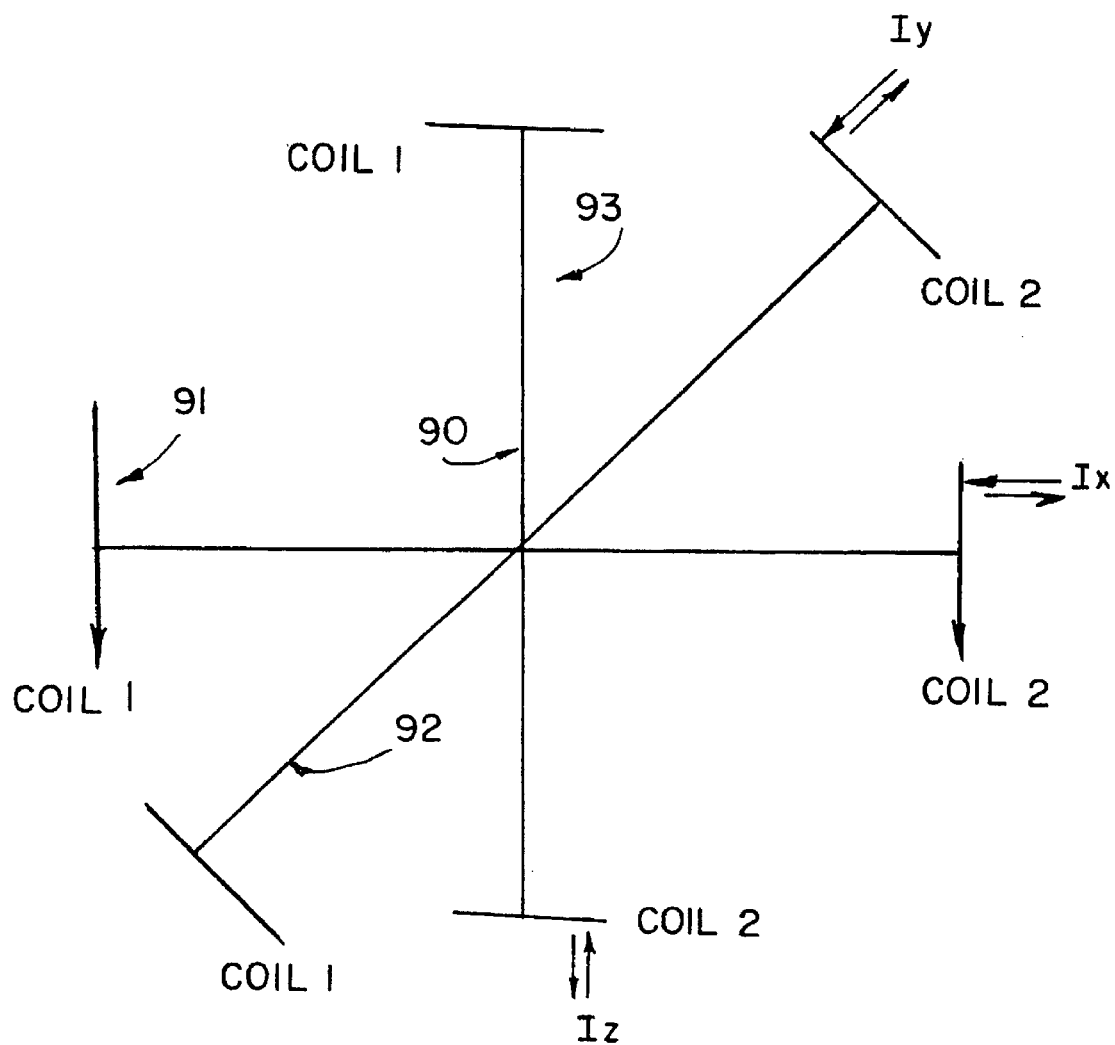
FIG. 5 is a schematic representation of the axes.

5. From the seed position 41 given by the fluoroscopes 43, the algorithm calculates the current impulse 47 in each coil needed to supply its gradient impulse component 49. This employs results from the Direct Force Calculation (DFC) module used in reverse in a simple way. The Direct Force Calculation is based on well-known electromagnetic equations. From this point on we will drop the terms "impulse" for current, gradient and force, although it is always implied:

(a) It assumes the magnetic object is on the axis for each coil's 91 contribution, as shown in FIG. 5. FIG. 5 also shows intersecting axes 90, 92, 93.

(b) An equation is written into the algorithm for the gradient of the coil as a function of the distance from the coil mid-plane, when there is full rated current in the coils. The equation 45 compares Gradient per 100 A Force mod curve and provides an independent value of current for each main coil. Boost is ignored.

(c) Using the location from the fluoroscope images, for each coil this distance 51 is entered to give the gradient component 53 of that coil if it had full current in it.

(d) The required gradient component of each coil is divided by the value obtained in step 5(c) to give the fraction of full current needed for each coil.

(e) These three numbers then give the actual predicted currents 47, calculated to apply the required force impulse components 49 on the magnetic object to get the distance called for by the red arrow.

6. Given the calculated currents from step 5(e), the algorithm uses the DFC module to calculate the actual force components that will result from those currents, and thence to get the actual distance to be traveled. This is used in two ways:

(a) First, the magnitude of the actual force is divided by the magnetic moment 33 of the magnetic object to get the effective gradient 60 for a preliminary correction to the currents. By comparison 63 with the force magnitude g 64 from step 3, the under- or over-calculation 65 of the gradients by the Vector Method is evaluated and used to rescale 67 the currents 61. Thus the green arrow will have the correct length.

(b) Second, the rescaled currents 67 are used to calculate the actual force from the DFC module (again employing the magnetic moment of the magnetic object).

7. The actual force 69 on the seed is then used to calculate 71 the green arrow 73, showing where the seed will actually go given the currents that have been calculated and then rescaled.

8. At this point, the operator input is used for the second time. The operator compares 75 the red and green arrows, with three possible consequences 77:

(a) If they are similar enough, the operator presses the step execution button 79.

(b) If the operator wants to improve the agreement he can:
     (1) Change the currents 81 directly, 83 based on experience.
     (2) Rotate the red arrow in a manner known by experience to change the currents 82 so as to bring the green arrow around to the desired direction.

9. In either step 8(b)(1) or 8(b)(2), the complete process iterates from step 1 again. When the operator is satisfied with the green arrow, he presses the step execution button. The vector boost logic 85 supplies the output currents 87 to the controllers. After a short training period, it is surprising how quickly these steps can be iterated.

10. The issues of boost and halt are avoided until the latter stages, where a factor is applied to the gradients as calculated from the DFC force module. There is no impulse calculated or needed in the DFC module. The factor takes into account the time-dependence of the impulses.

11. The factor is different for each of the three coil axes, and depends on where the seed is located. A boost transfer function, determined by prior experiment, calculates the factor for each axis. Then the algorithm calculates the ramp time for each coil, using the peak boost current for that coil, and the voltage and inductance of that coil. This uses the standard equation $V=-L \, dI/dt$. With some current amplifiers this standard equation is replaced by more optimal functions.

12. The boost is applied automatically, without separate operator action.

The distance-to-force transfer function is constructed with data obtainable by direct experimentation, i.e. by calculable force-impulse distance data taken on axis of one set of coil pairs. In two places in the algorithm, the force-to-gradient conversion, in the vector approximation, is simply division by a number, which is the seed magnetic moment. For one magnetic object in use the magnetic moment is 0.01 A-m$^2$.

The incorporation of the above process and the red arrow part of the procedure into the software of this algorithm depends on details of successful inclusion of the fluoroscope vision in order to have the appropriate positional commands, whatever the state of calibration.

The arrow matching can be thought of as an iterative procedure. When the operator is satisfied, he presses the execute button. However, he has further control during the step. If, based on the fluoroscope observation the seed looks as if it will go too far, or in an incorrect direction, the halt mode can be invoked at any arbitrary time.

One addition to this method is the incorporation of an iterative self-corrective module which, since the steps are small, can use the difference between the observed and the called-for motion of the previous step as an error. That same error, to first order, can be assumed to apply to the next step unless a radical direction change is called for. When applied it will cause a correction in advance for the next step. Other improvements suggested by experience can be incorporated.

Sets of superconducting coils are operated for providing strong force impulses and accurate motion steps of a small magnetic object in the coils combined field, and minimizing the risk of quenching the coils. The operation includes the following steps:

(a) calculating currents of opposite directions in opposite members of a pair of the coils;

(b) providing appropriate ratios of the two currents of each opposite member of each pair of coils so that the magnetic element will be pulled in the correct direction with both a pulling force from a main coil and a pushing force from a supplemental coil in a coil pair, with appropriate values and timing so as to allow much stronger forces than from a single coil;

(c) reversing current in the supplemental coil so that it acts to retard motion of the magnetic object at an appropriate time so as to enhance the degree of control of the motion;

(d) using currents in any or all of six coils in three coil pairs, and creating a combined force of such a direction and of such a dependence on time as to give the magnetic element a required motion step;

(e) using currents in any or all of the six coils and responding to images obtained from rapid imaging at least several times a second, in a manner for giving the magnetic element a substantially continual force and, with a feedback, causing the element to follow a required path; and (f) using the superconducting coils in pairs so that the supplemental coil acts in a subsidiary manner, and with much smaller current, and still supplies significant, even a majority, of force with greatly decreased risk of quenching the coil.

Multiple pairs of coils, superconducting or otherwise, are operated in a manner to avoid the lack of specificity of specifying only the force magnitude and direction on a magnetic object. The following steps are included:

(a) providing a vector addition of the individual coil pair effects and generating an approximate assumption of required forces, capable of later correction;

(b) determining the vector components from input of an operator;

(c) using the vector components thus determined and providing an estimate of coil currents required in all the coils of the system;

(d) using the estimated currents and calculating the exact force impulse to be applied to the magnetic object;

(e) using the calculated exact force impulse and the initially called-for vector components and recalculating the coil currents for improving the estimate;

(f) using the improved current estimate for providing visual display of an exact motion step that will ensue;

(g) using the display of the exact motion step and comparing with the initially called-for step vector components and making corrections in the called-for vector components; and (h) using the actual error of one executed motion step and providing a prior correction for a next motion step to be called for.

While the invention has been described with reference to specific embodiments, modifications and variations of the invention may be constructed without departing from the scope of the invention, which is defined in the following claims.

We claim:

1. A method of operating plural sets of superconducting coils, comprising providing strong force impulses and accurate motion steps of a small magnetic object in a combined field of the sets of coils, and minimizing a risk of quenching the coils, including the following steps:

(a) calculating currents in opposite members of each pair of the plural sets of coils;

(b) providing ratios of the calculated currents of each opposite member of each pair of coils so that the magnetic object will be pulled in a desired direction and yet have both a pulling force from a main coil and a pushing force from a supplemental coil forming each pair of coil;

(c) reversing current in the supplemental coil for retarding a motion of the magnetic object at an appropriate time;

(d) using currents in any or all of the coil pairs in the plural sets of coils, and creating a combined force for imparting to the magnetic object a required motion step;

(e) using currents in any or all of the plural sets of coils and responding to images obtained from rapid imaging by giving the magnetic object a substantially continual force causing the element to follow a required path; and (f) using each of the plural sets of coils in pairs and allowing the supplemental coil in each pair to act in a subsidiary manner by providing a much smaller current such that the supplemental coil still supplies a significant force with greatly decreased risk of quenching the coil.

2. A method of operating plural pairs of coils, in a manner to avoid lack of specificity of specifying only the force magnitude and direction on a magnetic object, comprising:

(a) determining a vector addition of individual coil pair effects and generating calculations of required forces, said calculations being subsequently changeable;

(b) determining plural components of the vector from inputs of an operator;

(c) using the vector components thus determined and providing an estimate of coil currents required in all the coils of the system;

(d) using the estimated currents and calculating exact force impulse to be applied to the magnetic object;

(e) using the calculated exact force impulse and the vector components and recalculating the coil currents for improving the estimate;

(f) using the improved current estimate for providing visual display of an exact motion step that will ensue;

(g) using the display of the exact motion step and comparing with the vector components and making corrections in the vector components; and (h) using an actual error of one executed motion step and providing a correction for a next motion step prior to effecting the next motion step.

3. A magnetic stereotaxis system comprising a pair of spaced coils having a first, main, pulling coil and a second, subsidiary, pushing coil mounted at a spaced position from the first coil for establishing combined magnetic fields and gradients between the first and second coils, a magnetic object positioned in a media between the coils, a current in the first coil for producing a sub-threshold force for aligning the magnetic object in the media, which sub-threshold force is below a threshold force necessary to move the magnetic object through the media, a current supplied to the second coil for producing a boost force in combination with the sub-threshold force of the first coil as a combined force for exceeding the threshold force and producing movement of the magnetic object in the media, means for reversing the current in the second coil for providing a halt force for reducing the combined force to below the threshold force and for halting movement of the magnetic object in the media.

4. The apparatus of claim 3, further comprising means for reducing current in the main coil after the boost force for reducing force produced by the main coil to a sub-threshold force level as the magnetic object moves closer to the main coil.

5. The apparatus of claim 4, further comprising a second pair of coils having a main pulling coil and a subsidiary pushing coil for holding the magnetic object and moving the magnetic object in a different direction.

6. The apparatus of claim 5, further comprising a third pair of coils cooperating with the first and second pair of coils for holding and moving the magnetic object in another direction.

7. The apparatus of claim 6, wherein the three pairs of coils are arranged along mutually perpendicular axes for holding and moving the magnetic object in the media.

8. The apparatus of claim 7, further comprising a display for showing the position of the magnetic object in the media and for showing a vector of desired movement of the magnetic object in the media.

9. The apparatus of claim 8, further comprising a computer with an algorithm connected to the display for calculating the currents to be applied to the coils and for displaying a second vector of motion to be expected from calculated force impulse from the calculated currents.

10. The apparatus of claim 9, further comprising controls connected to the processor for changing the currents for changing the motion to be expected.

11. The method of controlling movement of a magnetic element in a media, comprising providing a first pair of spaced coils having a first main pulling coil and a second subsidiary pushing coil spaced from the first coil, providing a current in the first coil for providing from the first coil a sub-threshold force for holding the magnetic object in the media without moving the magnetic object through the media, providing a boost current in the second subsidiary coil for producing a boost pushing force additive with the sub-threshold force from the first coil for providing a total force in excess of the threshold force and moving the magnetic object in the media, providing a halt current in the subsidiary coil for producing a pulling halt force from the secondary coil which is subtractive from the pulling sub-threshold force of the first coil for stopping the magnetic object in the media.

12. The method of claim 11, further comprising reducing current in the first coil for reducing the sub-threshold force after the magnetic object moves toward the first coil.

13. The method of claim 12, wherein the boost current and the halt current are time-dependent currents.

14. The method of claim 13, wherein the boost current and halt current are separated by a time.

15. The method of claim 12, further comprising displaying on a display position of the magnetic object in the media, displaying a desired motion vector on the display, providing the desired movement to a processor with an algorithm, and providing to the display from the processor an expected motion vector.

16. The method of claim 15, further comprising adjusting expected currents to bring the expected motion vector into agreement with the desired motion vector and executing the currents in the subsidiary coil.

17. The method of claim 15, further comprising moving the desired motion vector on the display and thereby moving the expected motion vector from the processor toward an original position of the desired motion vector.

18. The method of claim 12, further comprising providing three pairs of spaced coils arranged in mutually perpendicular axes, each pair having a main pulling coil and a subsidiary pushing coil.

19. The method of claim 11, wherein the media is a body part and wherein the method further comprises placing the magnetic object in the body part.

20. The method of claim 19, wherein the body part is a brain.

21. A method of operating a pair of coils to move a magnetic object in soft body tissue, the method comprising the steps of:

(a) providing a first current in a first coil of the coil pair closer to the magnetic object; and (b) providing a second current in a second coil of the coil pair farther from the magnetic object, the second current providing a contribution to a magnetic field from both coils of the coil pair that is sufficiently small so that the magnetic object is pulled by a magnetic field from the first coil;

wherein the first and the second currents are provided to the coil pair in an anti-Helmholtz configuration.

22. The method of claim 21, further comprising the additional step of imparting a controlled impulsive force to the magnetic object by providing a short duration boost current in the second coil.

23. The method of claim 22, further comprising the additional step of pulling back the magnetic object by providing a third current in the second coil of opposite direction to the boost current.

24. The method of claim 21, further comprising operating three mutually perpendicular pairs of coils, wherein each pair of the mutually perpendicular pair is operated in accordance with the method of claim 21.

25. A method of moving a magnetic object in a body part to a specific location using a set of mutually perpendicular coil pairs controlled by a controller, the method comprising the steps of:

(a) determining a position of the magnetic object from biplanar fluoroscopic images;

(b) displaying the position of the magnetic object superimposed over an MR/CT scan;

(c) inputting a desired movement of the magnetic object to the controller;

(d) computing, from the desired movement input to the controller, an approximation of currents in the set of coil pairs needed to produce the desired movement using a vector method of calculation;

(e) computing an actual movement of the magnetic object from the computation of step (d);

(f) displaying the computed actual movement to the operator;

(g) inputting modifications of the approximate currents calculated in step (d) to the controller; and (h) moving the magnetic object by applying the modified approximate currents to the coils of the mutually perpendicular pairs of coils.

26. The method of claim 25, further comprising the step of selecting which ones of the coils in each of the mutually perpendicular pairs of coils is a first and a second coil in accordance with vector components of the desired movement input by the operator.

27. The method of claim 26, wherein the computation of the approximate currents includes the step of computing a force impulse required for the magnetic object to travel a distance specified by the desired movement in accordance with a DF transfer function.

28. The method of claim 27, wherein the computation of the approximate currents includes the step of computing a gradient impulse magnitude corresponding to a magnitude of the force impulse.

29. The method of claim 25, further comprising applying boost automatically, taking into account time-dependence of the impulses.

30. The method of claim 25, wherein step (d) further comprises calculating gradient impulse components based on coil coordinates of the desired movement input of step (c).

31. The method of claim 30, wherein the calculating of gradient impulse components further comprises calculating current impulse in each coil needed to supply the gradient impulse component by assuming the magnetic object is on an axis of contribution for each coil, wherein the gradient of each coil is provided as a function of distance of the magnetic object from the coil mid-plane, wherein each coil's gradient component is calculated as if that coil had full current, wherein the required gradient component of each coil is divided by the full current calculation to provide a fraction of full current needed for each coil, and wherein actual predicted currents for each coil are calculated to apply the force pulse components required on the magnetic object to provide the desired input movement of step (c).

32. The method of claim 31, wherein step (e) further comprises calculating actual force components that will result from the actual predicted currents, dividing the actual force components by magnetic moment of the magnetic object and providing an effective gradient for preliminary correction of the currents, and correcting the display of computed actual movement of step (f).

33. The method of claim 29, wherein step (g) further comprises comparing the desired movement input of step (c) with the computed actual movement of step (f).

34. The method of claim 33, further comprising changing the desired movement input and bringing the computed actual movement to the original desired movement input.

35. The method of claim 28, further comprising applying halt currents to the coils for retarding the magnetic object movement if the movement appears excessive or in an incorrect direction.

36. The method of claim 25, wherein step (g) is automatically accomplished according to a difference between observed and called-for motion of a previous step (h) in a previous movement of the magnetic object.

37. The method of controlling a movement of a magnetic object in a body, comprising viewing present magnetic object position in a body on a computer screen, inputting a desired vector position change for the object and showing the desired change on the screen as a red arrow, calculating magnetic forces on the magnetic object needed to move the object as indicated by the red arrow, calculating movement of the object in the body by the application of the magnetic forces and displaying the calculated movement on the screen as a green arrow, moving the red arrow on the screen and recalculating the forces and movement of the magnetic object for moving the green arrow to the original position of the red arrow and applying the recalculated forces to the object.

* * * * *